United States Patent [19]
Tracy et al.

[11] Patent Number: 5,837,668
[45] Date of Patent: Nov. 17, 1998

[54] ACYLOXYALKANE SULFONATE AND AMPHOTERIC SURFACTANT BLEND COMPOSITIONS AND METHODS FOR PREPARING SAME

[75] Inventors: David James Tracy, Plainsboro; Paul Frank D'Angelo, Princeton, both of N.J.

[73] Assignee: Rhodia Inc., Cranbury, N.J.

[21] Appl. No.: 641,124

[22] Filed: Apr. 30, 1996

[51] Int. Cl.$^6$ .............................. B01F 17/00; C11D 1/12
[52] U.S. Cl. ..................... 510/418; 510/456; 510/426; 510/489; 510/495; 252/351; 252/353
[58] Field of Search ..................... 510/418, 456, 510/426, 489, 495; 252/351, 353

[56] References Cited

U.S. PATENT DOCUMENTS

| | | |
|---|---|---|
| 2,697,872 | 12/1954 | Armstrong . |
| 3,429,136 | 2/1969 | Holt . |
| 4,102,826 | 7/1978 | Rnaud . |
| 4,235,758 | 11/1980 | Dawson et al. . |
| 4,307,009 | 12/1981 | Luders et al. ................ 260/42.14 |
| 4,316,824 | 2/1982 | Pancheri . |
| 4,435,317 | 3/1984 | Gerritsen et al. . |
| 4,436,647 | 3/1984 | Prison et al. ................ 252/358 |
| 4,515,721 | 5/1985 | Login et al. . |
| 4,596,672 | 6/1986 | MacDuff et al. . |
| 4,612,132 | 9/1986 | Wollenberg . |
| 4,671,894 | 6/1987 | Lamb et al. . |
| 4,680,143 | 7/1987 | Edge et al. . |
| 4,681,704 | 7/1987 | Bernardino et al. . |
| 4,696,767 | 9/1987 | Novakovic et al. ............ 252/557 |
| 4,732,704 | 3/1988 | Bierman et al. . |
| 4,790,956 | 12/1988 | Weipert et al. . |
| 4,823,635 | 4/1989 | Selby . |
| 4,853,147 | 8/1989 | Choi . |
| 5,096,622 | 3/1992 | Simion et al. . |
| 5,225,097 | 7/1993 | Kacher et al. ................ 252/112 |
| 5,225,098 | 7/1993 | Kacher et al. ................ 252/112 |
| 5,227,086 | 7/1993 | Kacher et al. ................ 252/112 |
| 5,238,609 | 8/1993 | Smith et al. . |
| 5,262,079 | 11/1993 | Kacher et al. ................ 252/112 |
| 5,269,974 | 12/1993 | Ofosu-Asante . |
| 5,298,195 | 3/1994 | Brumbaugh . |
| 5,300,665 | 4/1994 | Tracy et al. ................ 554/49 |
| 5,340,502 | 8/1994 | Palicka . |
| 5,384,421 | 1/1995 | Day et al. ................ 554/92 |
| 5,415,810 | 5/1995 | Lee et al. . |

*Primary Examiner*—S. Mark Clardy
*Assistant Examiner*—Sabiha N. Qazi
*Attorney, Agent, or Firm*—Paul J. Juettner; John Daniel Wood

[57] ABSTRACT

A process for preparing blends or slurries of acyloxyalkane sulfonate salts is provided. The salts have the formula:

$$R_1C(O)O(CH_2)_nSO_3Y$$

wherein $R_1$ is a hydrocarbyl radical having from about 6 to about 26 carbon atoms, n is an integer of from 2 to 4 and Y is an alkali metal or alkaline earth metal. The blend also comprises an amphoteric and/or anionic surfactant. The first step of the process comprises acylating an alkane sulfonic acid with a fatty acid at a temperature above about 180° C. forming a molten reaction mass of acyloxyalkane sulfonate salts. In the next step, the molten reaction mass is quenched in an aqueous quench liquid comprising an amphoteric and/or anionic surfactant. Finally, a blend comprising an acyloxyalkane sulfonate and an amphoteric and/or anionic surfactant is recovered.

22 Claims, No Drawings

ACYLOXYALKANE SULFONATE AND AMPHOTERIC SURFACTANT BLEND COMPOSITIONS AND METHODS FOR PREPARING SAME

BACKGROUND OF THE PRESENT INVENTION

The present invention relates to an improved process for preparing combinations of acyloxyalkane sulfonates and amphoteric and/or anionic surfactants in high purity and low salt content.

Acyl isethionates, broadly classed as acyloxyalkane sulfonates, are known ingredients useful in synthetic detergent bars (syndet bars), shampoos, body washes, bubble baths, creams and lotions. The preferred isethionate is sodium cocoyl isethionate (SCI).

The reaction of acid chlorides of carboxylic acids with 2-amino- or 2-hydroxyalkanesulfonic acids and their alkali metal salts to yield anionic surfactants (for example, sodium N-acyltaurates and sodium acylisethionates, respectively) is well known as the Schotten-Baumann synthesis.

The Schotten-Baumann chemistry is very laborious and costly, requiring the handling of hazardous raw materials such as phosphorus trichloride and intermediates like acid chlorides as well as wastes like phosphorus acid. Large quantities of waste products are generated as a result of this chemistry. Also, the finished products contain significant amounts of sodium chloride as an undesirable by-product. The removal of the sodium chloride is possible, but expensive.

Sodium acylisethionate synthesis has been greatly improved by the direct esterification of sodium isethionate with fatty acids. This direct esterification route is cost-effective and these products are suitable for use in commercial toilet soap and personal care preparations.

The preparation of such sulfonate esters by direct esterification of a hydroxyalkyl sulfonate with a fatty acid has presented difficulties because of the high temperature required to obtain suitable conversion. At temperatures required for direct esterification, usually in the range of 220° to 250° C., the molten reaction product rapidly degrades in color and loses activity. It has been found necessary to rapidly cool the reaction mass in order to obtain a high active final product. On method of quenching involves pouring the molten reaction mixture into a flaker. However, this method requires that the product be molten at the decomposition temperature for a long period of time before the material is allowed to flow into the flaker. Thus, there is a tradeoff on flowablity verses decomposition. In an alternative method, U.S. Pat. No. 3,429,136 teaches injecting cold water directly into the molten crude reaction mixture to cool the mass by evaporative cooling below a temperature at which rapid discoloration would occur and this can be done without causing appreciable hydrolysis of the ester.

Since the crude reaction product ordinarily contains unreacted fatty acid, sulfonate or both, various methods have been proposed for purification. Generally these methods comprise forming liquid systems in which the impurities are soluble and the product is insoluble. Following cooling, the soluble impurities can be separated with the liquid by filtration means.

U.S. Pat. No. 4,515,721 teaches that excess fatty acid can be removed from an isethionate reaction mixture by quenching the hot crude fatty acid ester by immersion in a liquid in which the desired ester product is insoluble and the unreacted fatty acid soluble. The phases are separated to affect purification. In this patent the isethionate can be quenched in various products including lower chain length alcohols, fatty alcohols, fatty alcohol ethoxylates, polyethylene glycols, polyoxyalkylene derivatives of polyethylene glycol, fatty triglycerides, fatty esters and fatty amides. The preferable quenching liquid is isopropanol.

U.S. Pat. No. 4,612,132 describes a process for preparing an aqueous surfactant solution and gel of an acyloxyalkane sulfonate salt by combining the sulfonate salt with a water soluble polyol and water. This mixture is heated above the boiling point of water under super atmospheric pressure to form a reversible solid colloidal solution from which the product can then be recovered. See also, U.S. Pat. No. 4,696,767.

When SCI is employed in conventional soap bar manufacture, SCI is added as a fine particulate solid to an agglomerator containing soap pellets or chips, known as the soap base. The SCI in this fine particulate phase, can induce sneezing, tearing and or coughing, and tends to be so readily transmitted in the atmosphere as to contaminate other products and compositions made in the same plant environment. While SCI is available in larger particle sizes, they are not capable of homogenization in the several processing stages employed in the manufacture of syndet bars.

SCI has limited solubility in water. While blends of SCI and aqueous solutions of surfactant can be made, they are of low SCI concentration if a liquid or in the form of a suspension or paste if of a higher SCI content. U.S. Pat. No. 5,415,810 discloses that blends of SCI and betaines (zwitterionics) can be made in an aqueous system where the zwitterionic surfactant assists in the dissolution of the isethionate.

It has now been discovered that acyloxyalkane sulfonate salts may be prepared in liquid, paste or gel forms containing various other surfactants in such a way as to avoid the disadvantageous properties of the SCI itself while performing the required process of quenching the molten material to form a stable product. Further, the problem of utilizing very fine particles is avoided along with the inherent environmental problems associated therewith.

SUMMARY OF THE PRESENT INVENTION

In accordance with the present invention, it has been discovered that improved aqueous detergent liquid, paste or gel compositions of acyloxyalkane sulfonates and amphoteric and/or anionic surfactants can be prepared while overcoming the numerous problems of the prior art with regard to the use of SCI mentioned in the preceding.

The surfactant composition of the invention is prepared by quenching a molten reaction mixture of the acyloxyalkane sulfonate in an aqueous solution of an amphoteric and/or anionic surfactant thereby reducing the temperature of the molten acyloxyalkane sulfonate below decomposition temperature, overcoming the problem of decomposition by eliminating extensive holding at high temperatures, greatly enhancing the solubility of the acyloxyalkane sulfonate and forming mixtures of acyloxyalkane sulfonates and amphoteric and/or anionic surfactants and other optional ingredients.. Preferably, the surfactant which is in the quenching liquid is an amphoteric surfactant, preferably a betaine and the acyloxyalkane sulfonate is preferably SCI. By this process, blends of surfactants can be made of materials which are normally utilized together in the final end use area such as syndet bars, liquid detergent compositions, body washes, dish liquids, shampoos and the like. The present process allows for the intimate mixture of the surfactants without the need to solidify or isolate the SCI such as by the use of flakers as presently known in the prior art and to avoid the use of finely divided SCI which must be used because of difficulties in homogenizing a blend of larger SCI flakes with other materials.

Further, high active SCI can be quenched in the surfactant-containing quench liquid at a faster rate than required for flaking thus avoiding the need for the addition of the excess fatty acid as a matrix to insure stability while still reducing decomposition.

DETAILED DESCRIPTION OF THE PRESENT INVENTION

The present invention relates to an aqueous surfactant solution or gel comprising an acyloxyalkane sulfonate salt of the general formula:

$$R_1\text{-}C(O)\text{—}O(CH_2)_n SO_3 Y$$

wherein $R_1$ is a hydrocarbyl radical, desirably from about 6 to about 26 carbon atoms, n is an integer of from 2 to 4, preferably 2 and Y is an alkali metal or alkaline earth metal, more particularly, sodium, potassium, lithium or magnesium and preferably sodium. The alkane portion of the sulfonates of Formula 1 for use herein includes ethylene and branched or unbranched propylene or butylene. The fatty alkyl moiety $R_1$ is a hydrocarbyl containing from about 6 to about 26 carbon atoms and preferably from about 6 to about 20 carbon atoms such as hexanoic, octanoic, decanoic, dodecanoic, lauric, behenic, palmitic, stearic, myristic, arachidic, oleic, linolenic, linoleic and the like including mixtures of the foregoing as in the particularly preferred cocoyl derivatives from coconut oil fatty acids. Fatty acids from natural sources are comprised of numerous fatty acids that all generally fall within the state carbon range. A small proportion of mono - or di - unsaturated fatty acid derivatives may be desirable to provide adequate foaming and solubility in blends containing the neat soap. Normally, the degree of unsaturation will not be less than about 2 or more than 12, when measured by iodine number. It will be observed in this context that the term "hydrocarbyl" is intended to embrace linear and branched aliphatic radicals that include alkyl, alkenyl, alkynyl, and alkadienyl moieties. Too large a proportion of unsaturation, tends to render the sulfonate susceptible to oxidative degradation. The preferred compounds are acyl isethionates, preferably cocoisethionates.

The acyloxyalkane sulfonates are prepared by the direct esterification of a hydroxyalkane sulfonic acid with a fatty acid. The reaction can be conducted using well documented procedures. Temperatures of reaction are sufficient to effect reaction and maintain the product molten but not sufficiently high to cause substantial decomposition under normal product working conditions. Temperatures within the range of from about 180° C. to about 250° C. have been found to be effective. Since excess fatty acid is used as solvent, the molten reaction mixture contains the desired product along with excess fatty acid and sulfonate reaction material impurities. The reaction is conducted for a period of time sufficient to achieve conversion but insufficient to allow substantial product degradation, for example from about 1 to about 8 hours.

In accordance with the invention, the molten reaction product is quenched in an aqueous solution of amphoteric and/or anionic surfactant at a rate sufficient to cool the reaction mass below degradation temperature.

Amphoteric/ Zwitterionic Surfactants.

Amphoteric surfactants useful in the invention can broadly be described as a surface active agent containing at least one anionic and one cationic group and can act as either acids or bases depending on pH. Some of these compounds are aliphatic derivatives of heterocyclic secondary and tertiary amines in which the aliphatic radical may be straight or branched and wherein one of the aliphatic substituents contains from about 6 to about 20, preferably 8 to 18, carbon atoms and at least one contains an anionic water-solubilizing group, e.g., carboxy, phosphonate, phosphate, sulfonate, sulfate.

Zwitterionic surfactants can be broadly described as surface active agents having a positive and negative charge in the same molecule which molecule is zwitterionic at all pHs. Zwitterionic surfactants can be best illustrated by betaines and sultaines. The zwitterionic compounds generally contain a quaternary ammonium, quaternary phosphonium or a tertiary sulfonium moiety. The cationic atom in the quaternary compound can be part of a heterocyclic ring. In all of these compounds there is at least one aliphatic group, straight chain or branched, containing from about 6 to 20, preferably 8 to 18, carbon atoms and at least one aliphatic substituent containing an anionic water-solubilizing group, e.g., carboxy, sulfonate, sulfate, phosphate or phosphonate.

Examples of suitable amphoteric and zwitterionic surfactants include the alkali metal, alkaline earth metal, ammonium or substituted ammonium salts of alkyl amphocarboxyglycinates and alkyl amphocarboxypropionates, alkyl amphodipropionates, alkyl monoacetate, alkyl diacetates, alkyl amphoglycinates, and alkyl amphopropionates wherein alkyl represents an alkyl group having from 6 to about 20 carbon atoms. Other suitable surfactants include alkyliminomonoacetates, alkyliminidiacetates, alkyliminopropionates, alkyliminidipropionates, and alkylamphopropylsulfonates having between 12 and 18 carbon atoms, alkyl betaines and alkylamidoalkylene betaines and alkyl sultaines and alkylamidoalkylenehydroxy sulfonates.

Particularly useful amphoteric surfactants include both mono and dicarboxylates such as those of the formulae:

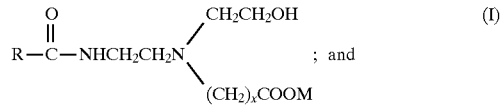

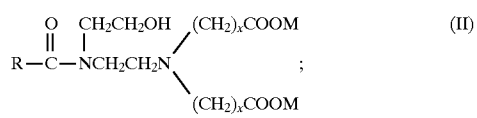

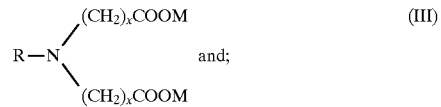

wherein R is an alkyl group of 6-20 carbon atoms, x is 1 or 2 and M is hydrogen or sodium. Mixtures of the above structures are particularly preferred.

Other amphoteric surfactants can be illustrated by the following formulae:

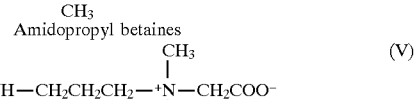

-continued

Alkyl sultaines

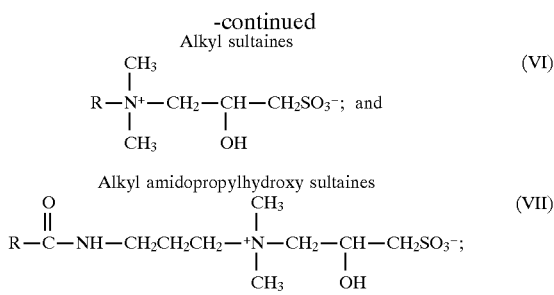

wherein R is an alkyl group of 6–20 carbon atoms.

Of the above amphoteric surfactants, particularly preferred are compounds wherein the alkyl group is derived from natural sources such as coconut oil or is a lauryl group. In reciting a carbon chain length range, it is intended to include groups such as coco which are naturally derived materials which have various specific chain lengths or an average chain length within the range.

Commercially useful and preferred amphoteric surfactants include (as sodium salts): cocoamphoacetate (sold under the trademarks MIRANOL® CM CONC. and MIRAPON® FA, and MIRANOL® ULTRA C-32 (preferred). cocoamphodiacetate (sold under the trademarks MIRANOL® C2M CONC. and MIRAPON® FB), cocoamphopropionate (sold under the trademarks MIRANOL® CM-SF CONC. and MIRAPON FAS), cocoamphodipropionate (sold under the trademarks MIRANOL® C2M-SF and MIRANOL® FBS), lauroamphoacetate (sold under the trademarks MIRANOL® HM CONC. and MIRAPON® LA), lauroamphodiacetate (sold under the trademarks MIRANOL® H2M CONC. and MIRAPON® LB), lauroamphodipropionate (sold under the trademarks MIRANOL® H2M-SF CONC. AND MIRAPON® LBS), lauroamphodiacetate obtained from a mixture of lauric and myristic acids (sold under the trademark MIRANOL® BM CONC.), and cocoamphopropyl sulfonate (sold under the trademark MIRANOL® CS CONC.).

Somewhat less preferred are: caproamphodiacetate (sold under the trademark MIRANOL® S2M CONC.), caproamphoacetate (sold under the trademark MIRANOL® SM CONC.), caproamphodipropionate (sold under the trademark MIRANOL® S2M-SF CONC.), and stearoamphoacetate (sold under the trademark MIRANOL® DM).

As used herein the term "ampho" is intended to refer to a structure derived from imidazoline chemistry. Various structures have been assigned to these products and the following are representative (x is as defined hereinbefore):

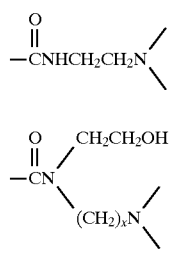

The quench liquid can also contain as the sole surfactant an anionic surfactant or the anionic surfactant can be coblended with an amphoteric surfactant during the quenching or after quenching.

Anionic Surfactants

Anionic surfactant detergents which may be included in the quench liquid used in the invention are those surfactant compounds which contain a long chain hydrocarbon hydrophobic group in their molecular structure and a hydrophilic group, including salts such as carboxylate, sulfonate, sulfate or phosphate groups. The salts may be sodium, potassium, calcium, magnesium, barium, iron, ammonium and amine salts of such surfactants.

Anionic surfactants include the alkali metal, ammonium and alkanol ammonium salts of organic sulfuric reaction products having in their molecular structure an alkyl, or alkaryl group containing from 8 to 22 carbon atoms and a sulfonic or sulfuric acid ester group. Examples of such anionic surfactants include water soluble salts of alkyl benzene sulfonates having between 8 and 22 carbon atoms in the alkyl group, alkyl ether sulfates having between 8 and 22 carbon atoms in the alkyl group and 2 to 9 moles ethylene oxide in the ether group. Other anionic surfactants that can be mentioned include alkyl sulfosuccinates, alkyl ether sulfosuccinates, olefin sulfonates, alkyl sarcosinates, alkyl monoglyceride sulfates and ether sulfates, alkyl ether carboxylates, paraffinic sulfonates, mono and di alkyl phosphate esters and ethoxylated deritives, acyl methyl taurates, fatty acid soaps, collagen hydrosylate derivatives, sulfoacetates, acyl lactates, aryloxide disulfonates, sulfosucinamides, naphthalene-formaldehyde condensates and the like. Aryl groups generally include one and two rings, alkyl generally includes from 8 to 22 carbon atoms and the ether groups generally range from 1 to 9 moles of ethylene oxide (EO) and/or PO, preferably EO.

Specific anionic surfactants which may be selected include linear alkyl benzene sulfonates such as decylbenzene sulfonate, undecylbenzene sulfonate, dodecylbenzene sulfonate, tridecylbenzene sulfonate, nonylbenzene sulfate and the sodium, potassium, ammonium, triethanol ammonium and isopropyl ammonium salts thereof. Particularly preferred sulfonate salt is sodium dodecylbenzene sulfonate. Such chemicals have been sold under the trade name Biosoft B100 by Stepan Chemicals of Northfield, Ill. Other anionic surfactants include polyethoxylated alcohol sulfates, such as those sold under the trade name Neodol 25-3S by Shell Chemical Company. Examples of other anionic surfactants are provided in U.S. Pat. Nos. 3,976,586 and 5,415,810. To the extent necessary, these patents are expressly incorporated herein by reference.

In addition to the amphoteric and/or anionic surfactants, the quench liquid used in the process of the invention can optionally comprise one or more of a nonionic or cationic surfactants as well as other optional ingredients.

Nonionic Surfactants

The quench liquid of the invention can optionally also include one or more nonionic surfactants. The nonionic surfactant(s) is not critical and may be any of the known nonionic surfactants which are generally selected on the basis of compatibility, effectiveness and economy.

Examples of useful nonionic surfactants include condensates of ethylene oxide with a hydrophobic moiety which has an average hydrophilic lipolytic balance (HLB) between about 8 to about 16, and preferably between about 10 and about 12.5. The surfactants include the ethoxylated primary or secondary aliphatic alcohols having from about 8 to about 24 carbon atoms, in either straight or branch chain configuration, with from about 2 to about 40, and preferably between about 2 and about 9 moles of ethylene oxide per mole of alcohol.

Other suitable nonionic surfactants include the condensation products of from about 6 to about 12 carbon atoms alkyl phenols with about 3 to about 30, and preferably between about 5 to about 14 moles of ethylene oxide. Examples of such surfactants are sold under the trade names Igepal CO 530, Igepal CO 630, Igepal CO 720 and Igepal CO 730 by Rhône-Poulenc Inc. Still other suitable nonionic surfactants are described in U.S. Pat. No. 3,976,586 which, to the extent necessary, is expressly incorporated herein by reference.

Cationic Surfactants

Many cationic surfactants are known in the art and almost any cationic surfactant having at least one long chain alkyl group of about 10 to 24 carbon atoms is suitable for optional use in the present invention. Such compounds are described in "Cationic Surfactants", Jungermann, 1970, incorporated herein by reference.

Specific cationic surfactants which can be used as surfactants in the invention are described in U.S. Pat. No. 4,497,718, incorporated herein by reference.

As with the nonionic and anionic surfactants, the compositions the invention may use cationic surfactants alone but preferably in combination with other surfactants as is known in the art. The composition of the invention can contain any useful amount but preferably up to about 20% by weight of surfactant actives based on the total surfactant actives weight in the quench liquid. Of course, the composition may contain no cationic surfactants at all.

pH Adjusting Chemicals pH adjusting chemicals such as acids, bases and buffers can be added to the quench liquid. Preferred pH adjusting chemicals include lower alkanolamines such as monoethanolamine (MEA) and triethanolamine (TEA). Sodium hydroxide solutions may be utilized as an alkaline pH adjusting agent. These solutions further function to neutralize acidic materials that may be present. Mixtures of more than one pH adjusting chemical can also be utilized.

Optional Ingredients

In addition to essential ingredients described hereinbefore, the quenching liquid of the present invention can also contain a series of optional ingredients which are used for known functionality at conventional levels.

The quenching liquid of the invention can contain phase regulants (well known liquid detergent technology). These can be represented by lower aliphatic alcohols having from 2 to 6 carbon atoms and from 1 to 3 hydroxyl groups, ethers of diethylene glycol and lower aliphatic monoalcohols having from 1 to 4 carbon atoms and the like.

Detergent hydrotropes could also be included. Examples of these hydrotropes include salts of alkylarylsulfonates having up to 3 carbon atoms in the alkyl group e.g., sodium, potassium, ammonium, and ethanolamine salts of xylene, toluene, ethylbenzene, cumene, and isopropylbenzene sulfonic acids.

Other supplemental additives include defoamers such as high molecular weight aliphatic acids, especially saturated fatty acids and soaps derived from them, dyes and perfumes; fluorescent agents or optical brighteners; anti-redeposition agents such as carboxymethyl cellulose and hydroxypropylmethyl cellulose; suspension stabilizing agents and soil release promoters such as copolymers of polyethylene terephthalate and polyoxyethylene terephthalate; antioxidants; softening agents and anti-static agents; photo activators and preservatives; polyacids, suds regulators, opacifiers, bacteriacide, and the like. Suds regulants can illustrated by alkylated polysiloxanes and opacifiers can be illustrated by polystyrene; bactericide can be illustrated by butylated hydroxytoluene.

Although not required, an inorganic or organic builder may optionally be added in small amounts to the final composition. Examples of inorganic builders include water-soluble alkali metal carbonates, bicarbonates, silicates and crystalline and amorphous alumino silicates. Examples of organic builders include the alkali metal, alkaline metal, ammonium and substituted ammonium polyacetates, carboxylates, polycarboxylates, polyacetyl, carboxylates and polyhydroxy sulfonates. One example of a commonly used builder is sodium citrate.

The optional ingredients, pH adjusting chemicals and optional surfactants can be added to the quenching liquid before, during or after quenching as desired or as practical. Blends can be made directly for sale or for compounding to meet the needs of the user.

The molten reaction mixture is added to the quench liquid at a rate sufficient to effectively cool the reaction mixture beneath the degradation temperature without over heating the quench liquid. Rate of addition, quantity, heat transfer capabilities as well as the total solids desired in the final product will control and these can be readily determined by one of ordinary skill in the art.

Quenching is conducted using good chemical manufacturing techniques. The molten reaction product is preferably transferred directly to a quench vessel containing the quench liquid but can be conducted through heated piping to maintain the reaction product in molten condition. The quench vessel is preferably equipped with an agitator and a cooling jacket. While a pressurized vessel could be use, this would require a pump to overcome the difference in pressure between the reaction vessel and the quench vessel while maintaining molten flow. The quench vessel is preferably equipped with a condensation means for condensing the water evaporated from the quench liquid during quenching. The condensate is preferably reintroduced into the quench liquid.

The molten material being quenched generally can contain from about 80% to about 95%, generally around 90%, actives, the remainder of the solids being impurities and reactants. The amount of actives depends on the efficiency of fatty acid removal from the reaction mixture. The molten material is added to sufficient quenching liquid to reduce the temperature of the reaction mixture below the decomposition temperature of the reaction product. Larger amounts of quench liquid can be desirable to absorb more heat. The amount of reaction product quenched is not a function of the degree of solubility of the reaction product in the quenching liquid. The amount of reaction product quenched could be above or below the solubility limit of the reaction product in the quenching liquid.

It is preferred that the total solids in the quenching liquid after quenching (not including solids added after quenching is complete) not exceed about 60%, preferably about 50% and more preferably about 45%. Included in the solids are the reaction product, the amphoteric or anionic surfactant, the optional surfactants, and the remaining optional ingredients including the pH adjusting chemicals. The ratio of reaction product to amphoteric and/or anionic surfactant can be expressed as ranging from about 85% - 15% reaction product to about 15% to about 85% amphoteric and/or anionic surfactant based on solids. It is preferable to use from about 40% to about 60% and from about 60% to about 40% and more preferably about 50% to about 50% reaction product to amphoteric and/or anionic surfactant.

When using a blend of amphoteric and anionic surfactants in the quench liquid, one can use from a negible amount of amphoteric surfactant to slightly less than 100% with the complementary ranges for the anionic surfactant. It is preferable to use from about 30% to about 70% amphoteric surfactant to about 70% to about 30% anionic surfactant on a solids basis and more preferably from about 45% to about 55% amphoteric surfactant to about 55% to about 45% anionic surfactant on a solids basis.

The nonionic surfactant based on total solids in the quenching liquid should not exceed about 20%; the cationic surfactant not more than about 10% of the solids and the optional ingredients not more than 10% of the total solids.

After quenching, the quenched material can be cooled and used as is or further purified such as by redissolving in a lower aliphatic alcohol, e.g., isopropanol. The product can be a pumpable liquid or a paste depending on the concentration of the ingredients. Higher levels of acyloxyalkane sulfonate lead to gels so that it may be desirable to use lower levels to prepare pumpable products.

The blends of the invention can be used directly in various personal care and household cleaning products or blended with further ingredients as desired. By this invention, blends of ingredients can be made using the product of the invention as a base.

The present invention will be more fully illustrated in the following non-limiting examples.

EXAMPLES 1–5

Reaction Equipment

The reaction kettle is an oil jacketed 4 necked 2 liter resin pot with a drip tip drain equipped with a mechanical stirrer, thermometer, nitrogen sparge, and Dean Starke trap leading to a reflux condenser. The kettle drain is connected to a 5 liter three neck round bottom flask equipped with a stirrer and reflux condenser.

Procedure

To the reaction kettle described above was added 339.4 grams (1.63M) coconut fatty acid 1.2 grams zinc oxide catalyst This reaction mixture was heated to 180°–200° C. with stirring under nitrogen purge. Over 1 hour 290.4 grams (55% solids, 1.08M) aqueous sodium isethionate solution was then charged.

After addition was complete, the reaction mixture was heated to 230° C. and held for 2 hours until water evolution ceased. 150 grams water was removed. Excess coconut fatty acid was removed by vacuum distillation. Removal of 100 grams of fatty acid resulted in a product 88% active by methylene blue analysis containing 7% coconut fatty acid. The product at approximately 180°C.–200° C. was drained into the 5 liter flask containing an aqueous solution of cocoamidopropylbetaine (1325 grams cocoamidopropylbetaine—MIRATAINE® CABA at 35% solids and 950 grams water). The product was a viscous liquid.

Various compositions were prepared in like manner and are tabulated as follows:

TABLE I

| EXAMPLE Ingredient | 1 Wt. % | 2 Wt. % | 3 Wt. % | 4 Wt. % | 5 Wt. % |
|---|---|---|---|---|---|
| Na Cocoyl isethionate | 15 | 20 | 30 | 20 | 30 |
| Water | 35 | 30 | 20 | 30 | 20 |
| Cocoamido propyl-betaine* (35% Solids) | 50 | 50 | 50 | — | — |
| Na Cocoampho-acetate** (% solids) | — | — | — | 50 | 50 |
| Observations | | | | | |
| Physical Appearance | Viscous Liquid | Paste | Paste | Viscous Gel | Paste |
| Viscosity | 9400 cPs | | | 92000 cPs | |

*MIRATAINE CABA
**MIRANOL ULTRA C-32
MIRATAINE & MIRANOL are trademarks of Rhône-Poulenc Inc.

What is claimed is:

1. A process for preparing blends or slurries of acyloxyalkane sulfonate salts of the formula:

$$R_1C(O)O(CH_2)_nSO_3Y$$

wherein $R_1$ is a hydrocarbyl radical having from 6 to 26 carbon atoms, n is an integer of from 2 to 4 and Y is an alkali metal or alkaline earth metal with amphoteric surfactants comprising (a) acylating hydroxylkane sulfonic acid with a fatty acid at a temperature above about 180° C. forming a molten reaction mass of acyloxyalkane sulfonate salts, (b) quenching said molten mass in an aqueous quench liquid comprising an amphoteric and/or anionic surfactant, and (c) recovering the blend comprising acyloxyalkane sulfonate and amphoteric and/or anionic surfactant.

2. A process as recited in claim 1, wherein $R_1$ has a carbon chain length ranging from about 6 to about 18.

3. A process as recited in claim 1, wherein $R_1$ is cocoyl.

4. A process as recited in claim 1 wherein n is two.

5. A process as recited in claim 1, wherein Y is sodium.

6. A process as recited claim 1, wherein said amphoteric surfactant is selected from the group consisting of the alkali metal, or alkaline earth metal salts of alkylamphocarboxyglycinates, alkylamphocarboxypropionates, alkylamphodipropionates, alkylamphomonoacetates, alkylamphodiacetates, alkylamphoglycinates and alkylamphopropionates wherein the alkyl represents an alkyl group having from 6 to 20 carbon atoms, alkyliminoacetates, alkyliminodiacetates, alkyliminopropionates, alkyliminodipropionates and alkyl amphopropyl sulfonates wherein alkyl represents an alkyl group having between 12 and 18 carbon atoms, and alkyl betaines, alkylamidoalkylene betaines, alkyl sultaines and alkylamidoalkylene hydroxy sultaines wherein alkyl represents an alkyl group from 6 to 20 carbon atoms and mixtures thereof and alkylene represents a carbon chain of from 2 to 4 carbon atoms.

7. A process as recited in claim 6, wherein alkyl represents a lauryl or coco group.

8. A process as recited in claim 1, wherein said amphoteric surfactant is a betaine.

9. A process as recited in claim 8, wherein said betaine is an amidopropylbetaine.

10. A process as recited in claim 8, wherein said betaine is cocamidopropylbetaine.

11. A process as recited in claim 1, wherein said amphoteric surfactant is an acylamphoacetate salt.

12. A process as recited in claim 1, wherein said quench liquid after quenching comprises not more than about 60% total solids by weight and the ratio of acyloxyalkane sulfonate to amphoteric and/or anionic surfactant on a solids basis ranges from about 85% to about 15% sulfonate to from about 15% to about 85% surfactant on a solids basis.

13. A process as recited in claim 1, wherein said quenching liquid further includes up to about 20% by weight nonionic surfactant on a solids basis.

14. A process as recited in claim 1, wherein said anionic surfactant is selected from the group consisting of water soluble salts of alkyl benzene sulfonates having between 8 and 22 carbon atoms in the alkyl group, alkyl ether sulfates having between 8 and 22 carbon atoms in the alkyl group, and alkali metal, salts of organic sulfuric reaction products having in their molecular structure an alkyl, or aralkyl group containing from 8 to 22 carbon atoms and a sulfonic or sulfuric acid ester group and mixtures thereof.

15. A process as recited in claim 1, wherein said anionic surfactant is selected from the group consisting of linear sodium and potassium alkyl ether sulfates that are synthesized by sulfating a higher alcohol having between 8 and 22 carbon atoms and having from 2 to 9 moles of ethylene oxide and alkyl benzene sulfonates in which the alkyl group contains between 9 and 15 carbon atoms, and mixtures thereof.

16. A process as recited in claim 1, wherein said anionic surfactant is selected from the group consisting alkyl sulfosuccinates, alkyl ether sulfosuccinates, olefin sulfonates, alkyl sarcosinates, alkyl monoglyceride sulfates and ether sulfates, alkyl ether carboxylates, paraffinic sulfonates, mono and di alkyl phosphate esters and ethoxylated deritives, acyl isethionates, fatty acid soaps, collagen hydrosylate derivatives, sulfoacetates, acyl lactates, aryloxide disulfonates, sulfosucinamides, naphthaleneformaldehyde condensates and the like wherein aryl groups include one and two rings, alkyl includes from 8 to 22 carbon atoms and the ether groups range from 1 to 9 moles of ethylene oxide.

17. A process as recited in claim 1, wherein said combined amphoteric and anionic surfactant comprises from about 30% to about 70% amphoteric surfactant to about 70% to about 30% by weight anionic surfactant on a solids basis.

18. A process as recited in claim 13, wherein said nonionic surfactant is selected from the group consisting of condensation products of primary aliphatic alcohols having from 8 to 24 carbon atoms, in either straight or branch chained configuration, with from 2 to 40 moles of ethylene oxide per mole of alcohol and condensation products of from 6 to 12 carbon atoms alkyl phenols with from 3 to 30 moles of ethylene oxide and mixtures thereof.

19. A process as recited in claim 1, wherein said quench liquid further comprises between about 0 and about 10% by weight of the quench liquid of supplemental additives selected from the group consisting of defoamers, dyes, perfumes, fluorescent agents, optical brighteners, antiredeposition agents, suspension stabilizing agents, soil release promoters, antioxidants, softening agents, antistatic agents, photoactivators, preservatives, inorganic builders, organic builders, additional enzymes, additional enzyme stabilizers, and mixtures thereof.

20. A process for preparing blends of acyl esters of isethionic acid salts and amphoteric and/or anionic surfactants comprising (a) reacting sodium isethionate with acylating agent, heating the blend to a temperature effective for reaction above about 180° C. for a period of time sufficient to effect reaction to form a molten reaction mixture, and (b) quenching the so heated molten reaction mixture in an aqueous solution of amphoteric and/or anionic surfactant.

21. A process as recited in claim 20, wherein said amphoteric surfactant is selected from the group consisting of the alkali metal or alkaline earth metal salts of alkylamphocarboxyglycinates, alkylamphocarboxypropionates, alkylamphodipropionates, alkylamphomonoacetates, alkylamphodiacetates, alkylamphoglycinates and alkylamphopropionates wherein the alkyl represents an alkyl group having from 6 to 20 carbon atoms, alkyliminoacetates, alkylimnodicetates, alkyliminopropionates, alkyliminodipropionates and alkyl amphopropyl sulfonates wherein alkyl represents an alkyl group having between 12 and 18 carbon atoms, and alkyl betaines, alkylamidoalkylene betaines, alkyl sultaines and alkylamidoalkylene hydroxy sultaines wherein alkyl represents an alkyl group having from 6 to 20 carbon atoms and mixtures thereof and alkylene represents a carbon chain of from 2 to 4 carbon atoms.

22. The product of the process of claim 1 wherein said aqueous quench liquid is comprised of an amphoteric surfactant.

* * * * *

UNITED STATES PATENT AND TRADEMARK OFFICE
CERTIFICATE OF CORRECTION

PATENT NO. : 5,837,668
DATED : November 17, 1998
INVENTOR(S) : Tracy, et. al.

It is certified that error appears in the above-identified patent and that said Letters Patent is hereby corrected as shown below:

In column 6, at line 21, delete "deritives" and insert therefore
--derivatives--

In claim 16, at line 7, delete "deritives" and insert therefore
--derivatives--

In claim 16, at line 7, after "deritives", delete "acyl isethionates" and insert --acyl methyl taurates--

Signed and Sealed this

Twenty-first Day of September, 1999

Attest:

Q. TODD DICKINSON

*Attesting Officer*      *Acting Commissioner of Patents and Trademarks*